US008612454B2

(12) United States Patent
Charles et al.

(10) Patent No.: US 8,612,454 B2
(45) Date of Patent: Dec. 17, 2013

(54) METHOD AND SYSTEM FOR PERSONALIZED HEALTH MANAGEMENT BASED ON USER-SPECIFIC CRITERIA

(76) Inventors: Dianne Charles, Galesburg, MI (US); Benjamin J Keller, Ann Arbor, MI (US)

( * ) Notice: Subject to any disclaimer, the term of this patent is extended or adjusted under 35 U.S.C. 154(b) by 0 days.

(21) Appl. No.: 12/592,114

(22) Filed: Nov. 19, 2009

(65) Prior Publication Data

US 2010/0145953 A1    Jun. 10, 2010

Related U.S. Application Data

(60) Provisional application No. 61/199,791, filed on Nov. 19, 2008.

(51) Int. Cl.
*G06F 17/30* (2006.01)
(52) U.S. Cl.
USPC .............................. 707/748; 707/802; 705/2
(58) Field of Classification Search
None
See application file for complete search history.

(56) References Cited

U.S. PATENT DOCUMENTS

| 2003/0158756 | A1* | 8/2003 | Abramson | 705/3 |
| 2005/0032066 | A1* | 2/2005 | Heng et al. | 435/6 |
| 2008/0015894 | A1* | 1/2008 | Miller et al. | 705/2 |
| 2008/0201174 | A1* | 8/2008 | Ramasubramanian et al. | 705/3 |
| 2010/0113892 | A1* | 5/2010 | Kaput et al. | 600/301 |
| 2010/0287213 | A1* | 11/2010 | Rolls et al. | 707/803 |

* cited by examiner

*Primary Examiner* — Yuk Ting Choi
(74) *Attorney, Agent, or Firm* — Law Offices of Indu M. Anand; Indu M. Anand, Esq.

(57) ABSTRACT

The present invention relates to dispensation of health care, specifically to personalized management of an individual user's health care. The invention presents a method of integrating personal risk analysis of the user as well as the resources utilized by the health care industry, including insurers, medical services providers and manufacturers, care givers and other participants in the user's health care decision making. Utilizing various filters with specific and known health risk factors and user preference models for the individual consumer, the system and method of this invention provide comprehensive information, including products and services of interest to the consumer, user community or another one of interested parties listed above.

11 Claims, 9 Drawing Sheets

CONCEPT

LIFESTYLE QUIZ  RISK PROFILE  GUIDELINES

FIG. 1 -- Risk based recommender

| Risk Factor | CH - Lifestyle Quiz Measurement* | Framingham Risk Score** | Framingham Cohort Measurement |
|---|---|---|---|
| Smoking | • *Have you smoked 10 or more cigarettes over the past year?*<br>• Dichotomous (Yes or No)<br>• Yes=1.40; No=1.0 | • Dichotomous<br>• Yes=2; No=0 | • Measured in # of cigarettes<br>• Also expressed in pack-years |
| Sedentary Lifestyle | • *Do you sit most of the time?*<br>• Dichotomous (Yes or No)<br>• Yes=1.49; No=1.0 | • Not in prediction model | • Framingham Physical Activity Index (24 hr recall instrument) |
| Family History CVD | • *Have either parent had an MI, heart disease, stroke or CABGS?*<br>• Dichotomous (Yes or No)<br>• Yes=1.28; No=1.0 | • Not in prediction model | • Medical history data |
| Diabetes | • *Has your doctor ever told you that you have diabetes or sugar in your blood or urine?*<br>• Self-reported<br>• Dichotomous (Yes or No)<br>• Yes=1.30; No=1.0 | • Dichotomous<br>• Yes=2; No=0 | • Physician diagnosed<br>• Fasting blood glucose>126 mg/dL |
| LVH | • *Has your doctor ever told you that you have an enlarged heart?*<br>• Dichotomous (Yes or No)<br>• Yes=2.00; No=1.0 | • Not in prediction model | • Physician diagnosed |
| Body Weight | • *Do you weigh more than the weight listed for your height and frame size?*<br>• Sex-specific tables<br>• Requires guess at body frame size (i.e., small, medium or large)<br>• Uses 120% of desirable weight for height as the risk threshold<br>• Dichotomous (Yes or No)<br>• Yes=1.32; No=1.0 | • Not in prediction model | • Medical examination<br>• Raw data for body weight<br>• Body mass Index (Kg/Ht squared)<br>• Weight/hip ratio |

FIG. 4A Part of replacement sheet for FIG. 4

| Risk Factor | CH - Lifestyle Quiz Measurement* | Framingham Risk Score** | Framingham Cohort Measurement |
|---|---|---|---|
| Hypertension | • *Have you ever been diagnosed as having high blood pressure?*<br>• Dichotomous (Yes or No)<br>• IF YES - uses age-adjusted coefficient regardless of SBP measurement<br>• IF NO - uses age-correction factor from Table 1.2 based on measured SBP<br>• Assumes SBP range of 140-149 if true value is not known | • Graded weighting of both SBP & DBP, with most abnormal value used in prediction model<br>• DBP categories: <80; 80-84, 85-89; 90-99 & ≥100<br>• SBP categories: <120; 120-129, 130-139; 140-159 & ≥160<br>• Categories weighted as -3; 0,1,2,3 for men, and -3, 0, 0, 2, 3 for women | • Raw data for SBP & DBP |
| Lipids | • *Do you know your cholesterol level?*<br>• Uses age-correction factor for 5 mg% intervals beginning with <185 mg%<br>• Assumes TC of 216-220 if true value is not known. | • Graded weighting of Total Cholesterol of LDL-C, and HDL-C<br>• Gender-specific weightings | • Raw data for all lipids |

FIG. 4B Part of replacement sheet for FIG. 4

LIFESTYLE QUIZ

What is your weight?  190
*Please enter your weight in pounds.*

Do you smoke?  ◯ Yes ⦿ No
*Answer the question yes if you have smoked 10 or more cigarettes per day over the past year.*

Do you sit most of the time?  ◯ Yes ◯ No
*Answer the question no if you exercise 3 times per week for 1/2 hour or more session.*

Do you have a family history of heart problems?  ◯ Yes ◯ No
*Answer the question yes if either of your parents had a heart attack, heart disease, stroke, or coronary bypass surgery.*

Has your doctor ever told you that you have diabetes?  ◯ Yes ◯ No
*Answer this question yes if your doctor ever told you that you have diabetes or sugar in your blood or urine.*

Has your doctor ever told you that you have an enlarged heart?  ◯ Yes ◯ No
*Answer this question yes if your doctor ever told you that you have an enlarged heart.*

Have you ever been diagnosed as having high blood pressure?  ◯ Yes ◯ No
*Answer this question yes if your doctor ever told you that you have high blood pressure.*

What is your Systolic Blood Pressure?  | 0 |
*Your systolic blood pressure is the top number in your blood pressure. If you don't know your blood pressure, leave it blank and averages will be supplied.*

What is your Cholesterol?  | 0 |
*If you don't know your cholesterol, leave it blank and averages will be supplied.*

FIG. 5A shows enlargement of Lifestyle Quiz in Fig. 5

QUIZ RESULTS

Age    Exercise    Family History    Blood Pressure    Smoking

Guideline

Recommended frequency and duration of exercise is 30 minutes or more every day or almost every day of the week.

Benefits

Exercise improves arterial function, decreases arterial inflammation (associated with heart attack and formation of blockages), increases muscle strength and endurance, lowers cholesterol and triglyceride levels and raises HDL, promotes weight loss, prevents or relieves back pain, alleviates stress, increases self confidence, prevents and alleviates anxiety and depression and reduces health care costs.

Show Me...
What's available...
What others like...
Groups...

FIG. 6

METHOD AND SYSTEM FOR PERSONALIZED HEALTH MANAGEMENT BASED ON USER-SPECIFIC CRITERIA

CROSS-REFERENCE TO OTHER APPLICATIONS

This application claims priority from the Provisional Patent Application, No. 61/199,791, filed by the same inventors on Nov. 20, 2008. The entire contents of the provisional application are incorporated herein by reference.

No new matter beyond the disclosure of the provisional applications has been introduced herein.

FIELD OF INVENTION

The present invention relates generally to dispensation of health care, and specifically to the management of an individual user's health care; the invention relies on a method of integrating personal risk analysis of the user as well as the resources utilized by the health care industry, including insurers, medical services providers and manufacturers, care givers and other participants in the user's health care decision making.

BACKGROUND AND PRIOR ART

The recent imperative of efficiency in the delivery of health care has generated a need and strong interest in consumer driven health plans, in which the premiums, contributory payment and other costs may be based on an array of factors, including the individual consumer's status of health and on their assumption and assessment of health risks. In this environment, it is important to understand and quantify differences in health status when analyzing the cost efficiency of different health plans for the purpose of establishing employee contribution requirements.

In such "user-centric" or "patient-centric" schemes, it is important for the individual consumers to have control on their health care decisions based on informative health guidelines. The general-purpose guidelines, when available, may not be interpreted by the users correctly, may be inapplicable to a particular consumer, or worse, may be harmful for their personal risk-profile.

Hence, there exists a need for a reliable system for personalized health guidelines incorporating users' health risks and other relevant information for the consumer to make informed decisions.

Providers of health plans, on the other hand, can use such a system to contain costs through the use of timely interventions, especially in the case of chronic disease; their key requirement is a reliable means to identify and categorize user needs based on their individual health risks.

There are many "users" with an interest in a health management system, including individual consumers, payers, health professionals and manufacturers, suppliers and providers, and third party administrators of health products and services.

Since it is possible to make personalized health information available to the diverse types of user groups with the help of the new media, therefore the providers of information dissemination networks and media may also be thought of as a "user" group whose needs intersect those of other groups of users of the system.

Computer networks, including the Internet, offer unprecedented opportunity for customized health care management by making information interactively available; opportunity exists, therefore, to provide information interactively and under user's control not only for the health guidelines based on personal risk factors and health care management parameters but also peripheral information, such as, the products and services that can assist the user in following the guidelines.

The value of information related to the products and services available in the marketplace should not be minimized, since in many cases availability of the right product or service can make the difference between success and failure of health regimen and the patient's following of the medical recommendations. Appropriate dietary products, such as a sugar substitute for diabetes and gluten-free recipes for celiac disease, or behavioral support group in a neighborhood are but simple examples of such market based products and services.

A robust system incorporating access to all relevant information from one "under one roof" can be useful to the consumers of healthcare, where relevant information for the user's decision making is either stored in a searchable database within the system or importable on demand.

At the present time, there is no available system for health management that incorporates integration of comprehensive health related information with the market-based data of useful products and services.

The system of the present invention is designed to provide relevant information, derived from multiple sources, at the fingertips of the user, personalized based on their individual requirements utilizing interactive dialog and robust filtering mechanisms. It includes components that filter and elicit the relevant information for the diverse groups of users noted above based on their need and scope.

In particular, for the individual consumer the filters provide personalized information to be extracted and shared based on the filters under consumer's direction and control.

The system of this invention incorporates privacy safeguards, including components that verify the authenticity of the user and the scope of the user's authority for each transaction and, except where otherwise required by law, allows consumer to retain complete control of personalized data.

Some of the components of this invention have been proposed and described in the prior art by the present inventors and others, as listed below. The present invention, however, is the first to conceive an integrated approach as described below in Summary and Detailed Description sections. The relevant prior art references are as follows:

Van-Fulpen, D. C., *Guide To Contented Hearts: Cardiac Risk Management*. Kalamazoo, Contented Hearts, Inc., 1995.

Framingham Risk Score, Wilson, et. al., Prediction of coronary heart disease. *Circulation* 1998: 97; 1837-1847

Real Age research U.S. Pat. No. 6,269,339—Inventors: Silver; Charles (La Jolla, Calif.) Assignee: Real Age, Inc. (San Diego, Calif.) application Ser. No. 09/222,687 Filed: Dec. 29, 1998.

Goldfield, N., Averill, R., Eisenhandler, J., Steinbeck, B., and others. The Prospective Risk Adjustment System, Journal of Ambulatory Care Management, 1999, 22(2), 41-52.

Recommender Systems—Resnick, Varian

Jeff Roitman, et. al.—A New Model for risk Stratification and Delivery of Cardiovascular Rehabilitation Services in the Long-Term Clinical Management of Patients with Coronary Artery Disease. J Cardiopulmonary Rehabilitation 1998: 18:1-000 Stratification—Notes included here—can site literature if needed.

Cpt Codes: Counseling and/or risk factor reduction intervention 99401-99402 © AMA book.

BRIEF DESCRIPTION OF THE DRAWINGS

FIGS. 4A and 4B constitute a table of comparison of the risk factors for heart disease, showing the values for the example described in Detailed Description. This illustrative table gives the definitions for Risk Factors Common to the Contented Hearts LQ & Framingham Cohort, and displays data reproduced from Van-Fulpen, D. C., *Guide To Contented Hearts: Cardiac Risk Management*. Kalamazoo, Contented Hearts, Inc., 1995, and Framingham Risk Score: Wilson, et al Prediction of coronary heart disease. *Circulation* 1998: 97; 1837-1847.

FIG. 5A shows a legible enlargement of the column of "Risk Factors" of FIG. 5.

FIG. 6 shows an example of interactive display of product and services integrated with the recommendations and risk profiles.

SUMMARY OF THE INVENTION

Figure 1:
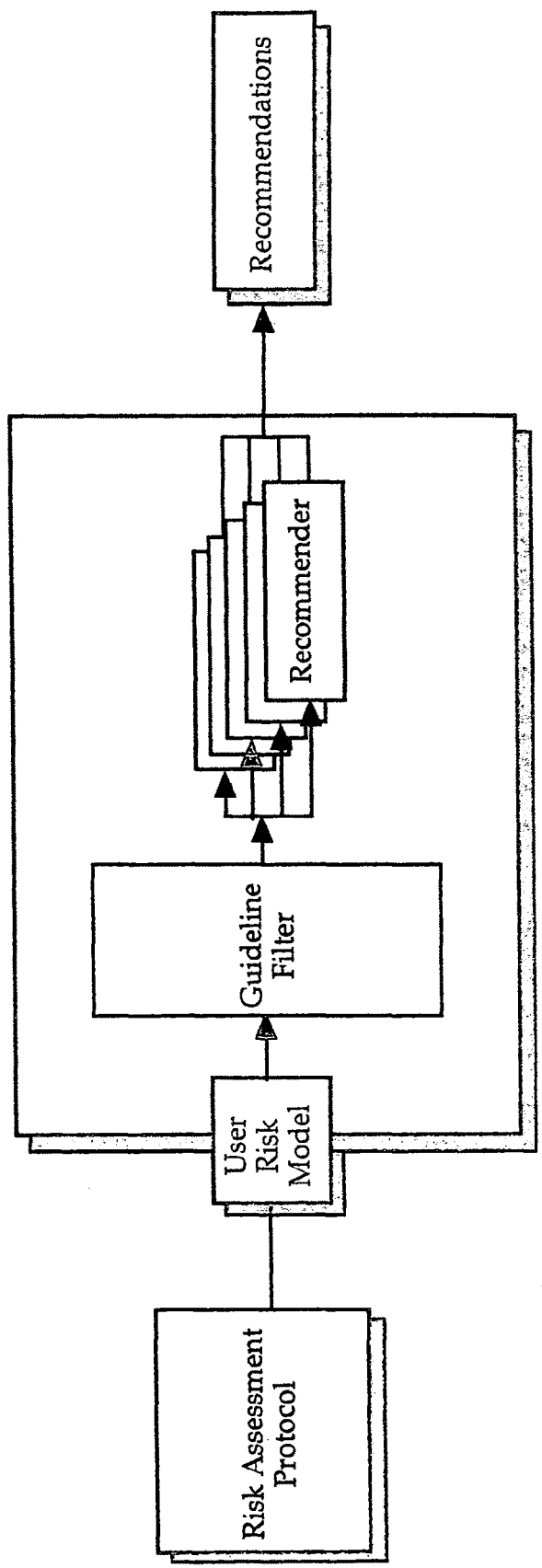
FIG. 1 is an illustration of the overall flow of risk assessment, filters for personalized evaluation and recommendations.

The present invention presents a method and a system to personalize or customize health care and health maintenance guidelines targeted to individual users. The components of the system include: databases incorporating general, validated and reliable health information; system components and criteria to carry out risk factor analysis for an individual patient's or user's risk assessment; as well as, a variety of classification and filtering algorithms from user preference models. It includes databases to facilitate ongoing analysis and reporting, and allows different users to make different risk-based decisions, set or assume different price structure for desired outcomes or customize the guidelines based on prospective risk analysis.

The system of this invention permits formation of groups of users for different risk categories based on personalized guidelines, including prospective risk-adjustment and payment methods that relate a user's risk profile to the amount, type, number and duration of services provided during the treatment of a specific disease process and prospective healthcare use category.

The universe of users of such an integrated, comprehensive system is diverse and includes individuals and groups—such as individual patients or consumers; health care payers; health professionals and manufacturers; suppliers, providers and third party administrators of health products and services. The service providers on Internet and other computer-based networks or other new media may also be expected to be interested parties in this view of health service dispensation.

A key aspect of the current system is a "recommender" component, which includes the mapping of products and services from categories that meet personalized guidelines for the individual consumer. This mapping may be stored within the recommender or provided by client software.

The method of verification of the private nature of the personalized guidelines sets apart the recommender system of this invention from the general purpose methods of recommendation used by vendors of other products and services or of general purpose merchandise.

Although focused on personalized health care management, the algorithms of the recommender of this invention may provide added value for the vendors of products and services, since it offers a unique mechanism to market the products and services in an individualized way to a particular consumer.

These recommendations may be refined, through the use of a "rating" algorithm by using information gathered from the community of users with the similar risk factors. For instance, by combining a user-provided rating for the products and services with other variables, we can generate a ranking of the products and services which may be more personally meaningful to each consumer or match their requirements. Using these virtual communities can help add further value of the system to the consumer, by placing them within a group with similar concerns, and the ability to use community based recommendations and the knowledge of other consumers to help make informed decisions.

As an illustration, provided in the description of the system of this invention is a detailed example incorporating a validated population based cardiac risk factor analysis algorithm for user risk clarification and a variety of classifier and filtering algorithms from user preference models.

One key purpose of the system is to make the health care and maintenance guidelines more readily acceptable to the users, thereby improving the follow through on those guidelines.

By making the recommendations integrated within the system, it is possible to dynamically fine-tune the recommendations for the end user. For instance, tools that allow tracking diet and exercise can benchmark the user's activity against the recommendations, and data entered by the user can be used to update the recommendations as risk factors change.

By using this critical feature of presenting the information in a dynamic, integrated fashion, it is possible to provide sustained value to the consumer.

DETAILED DESCRIPTION

The present invention provides a health care management method and system for integrated, user-centric, customizable, secure health care information dispensation with filters for dynamically updated individual context (including personalized risk assessment) for the purposes of efficiency, cost containment and compliance.

It is known that a major factor in successful healthcare management is the patient/client follow-through on guidelines and instructions supplied by a health professional. General guidelines along the lines of "lose weight" or "exercise" are often ambiguous and difficult to achieve.

Presented in this invention is a method and system to personalize user health guidelines, in combination with the personal risk factors, thereby clarifying the risk factors for the individual user; this system is integrated with user preference for the guidelines, along with the other aids that may help the user in the follow-through of the guidelines and recommendations.

The system and method further offer the capability of maintaining and presenting dynamically updated, personalized guidelines for the users which may be implemented using any of a number of modern media, including the Internet and other computer-based networks that have the capability to provide user-mediated, dynamic personalization of the data and guidelines periodically or on demand.

An example is a system that combines a prospective population based algorithm for risk factor assessment, including variables for diet and exercise, along with user preference modeling to help narrow the guidelines appropriate to the user's health profile at a particular moment in time and risks associated with specific actions—including diet and exercise.

The integration of user preferences with the risk-based recommendations within the system uses computer networks in a powerful new way and is calculated to encourage follow-through by making the recommendations more palatable to the user. User personalization of prospective risk may relate to the amount, type, number and duration of services—including exercise—and healthcare delivery use category, e.g. healthy, seriously ill, etc., in connection with the treatment of a specific disease process. Such details may allow users to personalize risk categories at various risk stages of a chronic disease process.

For total health management, the system is further integrated with information on products and services, with a capability to search and personalize this information relevant to the consumer' health status, risk profile, treatment and preferences.

The integration of all data relevant to the consumer's "total" health management is a new, and personally empowering and useful concept for the consumer. Coupled with careful implementation, the use of such a system offers the capability to improve compliance with health prescription, reduce errors and cut healthcare costs.

Often a major factor in healthcare client follow-through on guidelines is due to a lack of concrete steps to follow may effect follow through. By linking general strategies with specific risk recommendations in an interactive, personalized, risk-based "recommender," illustrated in FIG. 1, the present invention enables users to follow the health guidelines.

As an example of incorporation of user preference, consider the general guideline: "get more exercise."

The dose traditionally recommended for almost 25 years was: Exercise Dosage for Fitness: Frequency: 3 days/week-Duration: 30 to 45 minutes Intensity: moderate (heart rate range: 60-85% of maximum), Type: cardiovascular endurance exercise.

For a particular individual, however, the prescription may be better framed as follows: Dose for Health-related Exercise: Frequency: Daily or "almost every day"; Duration: 20-60 minutes; Intensity: Light to moderate activity, such as an activity involving more than sitting in a chair (walking, shopping, walking the dog, etc.).

This type of activity and/or exercise prescription (and the fitness dose) will work by improving follow-through and will yield health-related benefits, since increasing overall levels of "daily lifestyle activity" also contribute to reducing (heart related) events.

Figure 2:
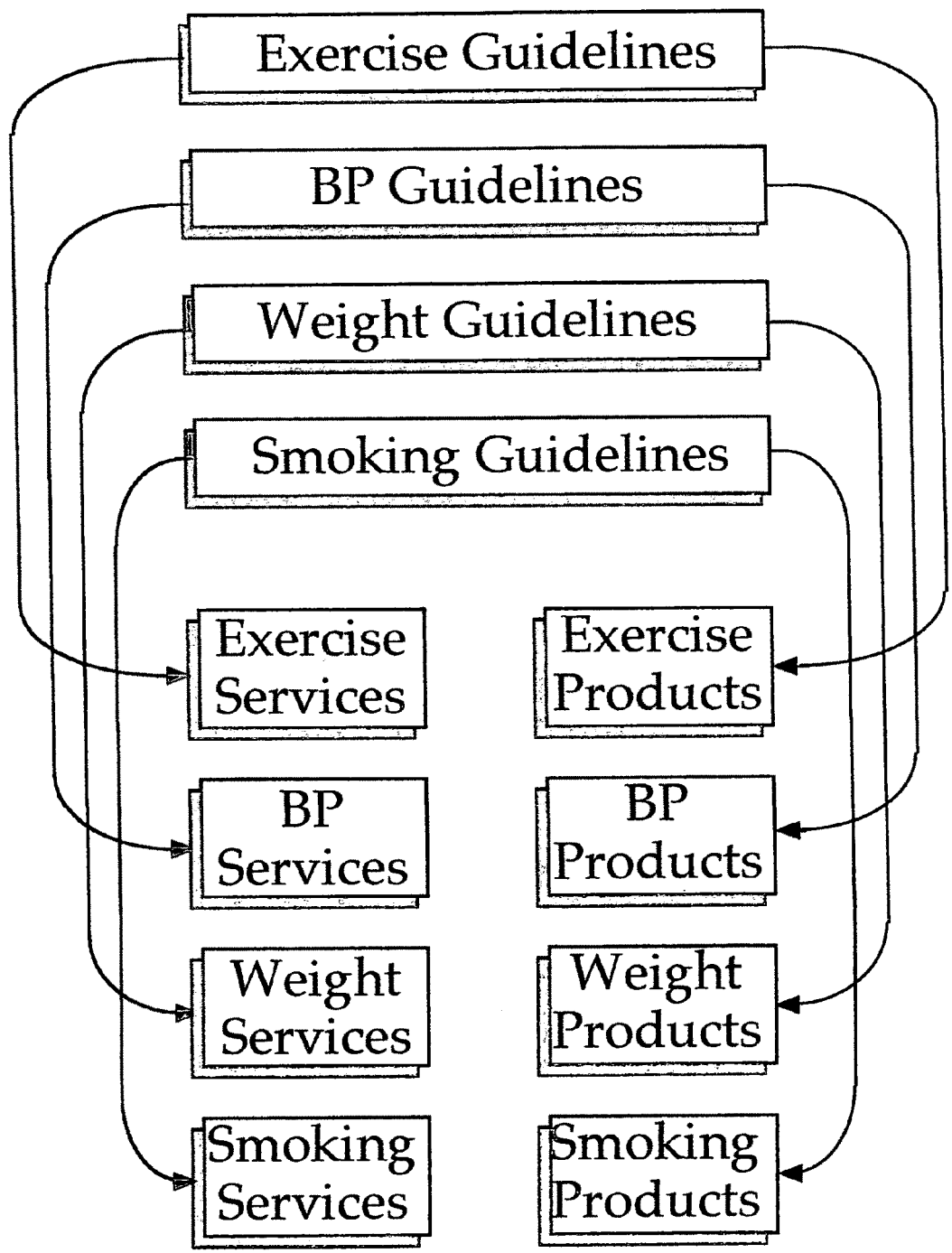
FIG. 2 shows an example of how guidelines and products and services may be linked in the system.

The system of the present invention is integrated with information on products and services, with the capability to search and personalize such information relevant to the consumer' health status, risk profile, treatment and preferences. FIG. 2 shows an illustration of the products and services which may be meaningful in this context. Such integration of all data relevant to the consumer's "total" health management is novel and, personally enabling and useful for the consumer. With a careful implementation, the use of such a system offers the capability to improve compliance with health prescription, reduce errors and cut healthcare costs.

Since the risk-based recommender system is conceived to include the database of user health-risk models and the encoded health guidelines, these recommendations are filtered based on risk-assessment as FIG. 1, and further interpreted in order to restrict the space of possible products and services to those in conformance with the guidelines.

The recommender system of this invention filters the space of products and services by employing one or more filters, or one or more types of specific recommenders that work within the general framework, in order to elicit recommendations tailored to an individual user's risk and preference models.

The use of distinct recommenders for different categories of decision items is provided to allow a more precise tailoring of the recommendations. For instance, a collaborative filtering approach may be more appropriate for exercise services or products, while a content-based filtering approach based on principle components analysis of food preferences and food item ingredients etc. may be more appropriate for recommendations based on dietary guidelines.

As stated above, the mapping of products and services into categories that meet the guidelines is a key, integral aspect of this system. This mapping may be stored within the recommender system or provided by, or imported from, external client software.

Thus, the recommender of the invention envisions, at a minimum, three distinct kinds of information integrated to provide tailored guidance to a user: First kind of information is the association of each risk factor with the corresponding medical recommendations; this includes, for example, a tailored set of behavioral and dietary guidelines to a user based on their individual risk factors. These recommendations may be automatically generated by the system, and filtered to present the individualized information.

Second kind of information relates to the products and services, presented in view of the particular medical recommendations. While the primary focus of this information is to provide readily usable information to the consumer, additionally it may be of interest to the vendors of the products and services, who may tailor the information for the preference group to which the consumer may belong. This approach can also add a valuable channel for marketers of the products and services.

Third, the system encompasses information of interest to a community of users with shared risk factors, disease status, preferences and goals etc. In particular, the recommendations can be refined using information gathered from a community of users with the same risk factors. For instance, by using consumer-provided ratings of the products and services, it may combine such information into a recommender system with enhanced value to the consumer Similarly, it may be advantageous to use virtual communities of consumers with similar concerns. Aside from providing the ratings, the virtual communities can assist in support and follow-through of the recommendations, and in making informed decisions.

The system of this invention is based on the concept that a dynamic integration of such diverse kinds of information is critical to the sustained value of the system to the consumer. For instance, tools that allow tracking diet and exercise can benchmark the user's activity against the recommendations, and data entered by the user can be used to update the recommendations as risk factors change or different products and services are utilized.

The total integration of all health-related information as described above achieves several objectives.

One object of the present invention is to provide a system and a method for enabling individual users and user groups to personalize risk-based health guidelines, and to present information regarding services and products most relevant to their risk category and later cost relevancy.

It is another object of the invention to provide a tool for cost-effective management, where a user or user group is charged fees in proportion to the number of actual risk categories.

For the clinician (nutritionist)/pharmacist or other medical service provider) the value of identifying and quantifying risk and risk factors is obvious. Advising and prioritizing appropriate treatments and intervention—including products and services—into those modifiable risk factors can significantly reduce the incidence of both first and subsequent catastrophic health events. A patient's risk factor analysis is a basic piece of the therapeutic puzzle that helps guide efficacious treatment.

Another object of the present invention to create a risk based category of users for outcomes where user groups target the most interested consumers by participating in an open market which attaches a monetary cost for a product and or service listing in a recommender user preference group list for guidelines generated using a health risk category group that tracks outcomes for groups.

It is yet another object of the present invention to create an open market that is fair to users who are consumers and suppliers, where supplier-placed listings for risk guidelines in a risk based Recommender/user preference risk category are clearly labeled as paid listing in a user group of groups of users.

Internet and other computer-based new media provide a way for suppliers to easily predict the position of their products and services for e-commerce using contextual advertising and sales but do not include a convenient method to gauge user preference. A tool enabling user groups to target products and services relevant to user preference, wants and needs benefits their business and to pinpoint the placement of products within the risk based recommender guideline results provides a powerful advantage to businesses and others seeking to increase to sell risk based products and services. Furthermore, a revenue sharing model based on number of user groups product and services sales generated by the risk based recommender helps ensure that the pricing structure reflects the market and is conveniently accessible to users of the system.

An important component of the system is the set of filters for comprehensive analysis of risk factors vis-á-vis other user data. Collaborative filters help find relevant content on the Internet, which unlike usual keyword search engines for the internet, actually gauges an individual's interest in content—in this case risk assessment. Risk based lifestyle recommendations with guidelines including diet and exercise use a form of content filtering. Further, content such as labels on cans or food items for health and reducing chronic conditions such as diabetes, high blood pressure and high cholesterol may be displayed for the user.

As an illustration of the integrated system of the present invention, detailed next is the specific case of heart disease.

The system of this example links the general health guidelines and specific recommendations combining user preference models and population based health risk factor analysis for personalization of health guidelines, including diet and exercise recommendations. The system persistently stores, for a single subject or a group of subjects, the results from each determination over time of the percentage absolute risk of having a heart attack (or having heart disease).

The system offers a basis for user profile formed by allowing the risk analysis of a clinical episode at the risk stage for heart disease. This example uses, in part, assignment of a Risk Adjustment Category ("RAC") which quantitatively represents severity of disease, for instance, a seven-digit number, where the first digit may indicate the individual's general health status among the following possibilities:

1) Healthy; 2) Moderate, Acute; 3) Single chronic; 4) Multiple Chronic; 5) Three or more Dominant Chronics; 6) Metastasic Malignancies; 7) Catastrophic Illnesses and Conditions.

The risk assessment for this example for a consumer is based on a population based algorithm that predicts for the user the risk of developing heart attack/heart disease based on the percentage of similarly situated population at risk of developing heart disease within ten years. This risk assessment incorporates the following risk factors: age, gender, chronic stress, high blood pressure, elevated cholesterol, smoking, excess weight, family history, lack of exercise, diabetes and enlarged heart.

A major advantage of making the exhaustive information, including sequential test results over time, available to the consumer for retrieval and display is to quantitatively demonstrate to the consumer the lowered risks associated with continuing healthy lifestyle choices and behavior changes.

Such demonstration of success to the user or user groups is possible because of personalization of risk guidelines for individuals. The individual users, and by extension, groups of users can receive the added advantage of motivating these users to follow the guidelines, reduce their risks and make behavioral changes.

Figure 5:
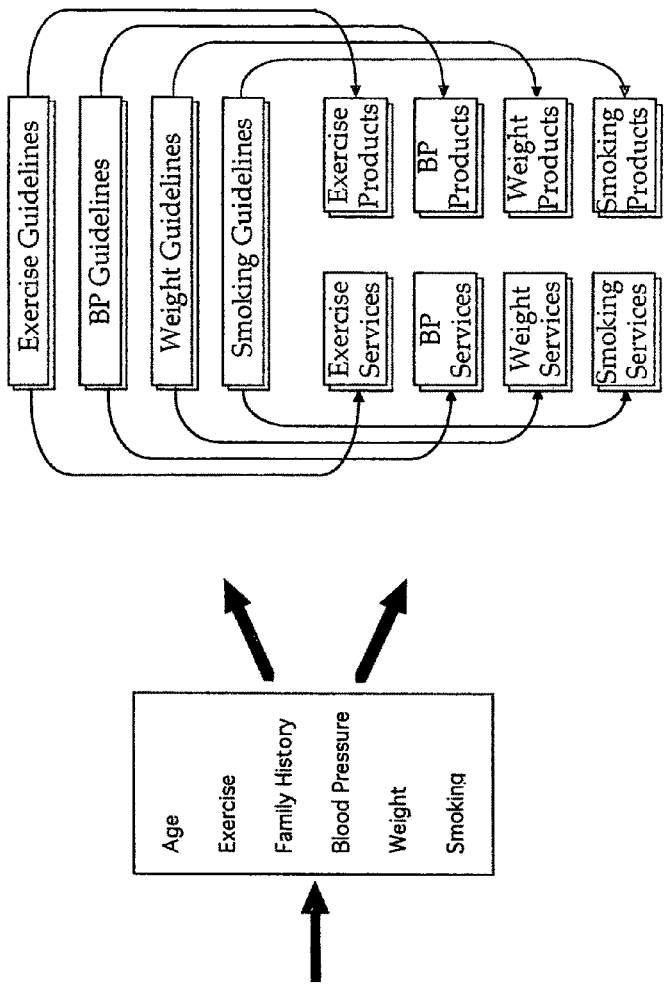
FIG. 5 depicts another illustration of overall flow of risk assessment, filters for personalized evaluation and recommendations.

The table in FIG. 4 presents the comparison of the tool used in this specific example, namely, The Lifestyle Quiz, shown in FIG. 5 and FIG. 6 in relation to user's risk profile and health guidelines, with the predictors of the well known, large population based Framingham Heart Study cited in prior art. Lifestyle Quiz computes the prediction values based on slightly different parameters from Framingham Heart Study, which parameters (including exercise) are easier to track from the typical user's point of view. The comparison table of FIG. 4 was prepared by a validation study conducted at Ball State University.

The system of this example uses the general health report profile for users of health risk status for a chronic condition or disease process and links general strategies with specific recommendations for personalization of health guidelines including products or services for individuals and groups.

The "user" groups for this example are varied.

In one embodiment a group is all subjects participating in a specific clinical practice.

In another embodiment a group is all subjects insured under a specific group medical insurance plan.

In another embodiment a group is all subjects insured in any group medical plan of a specific insurer.

In another embodiment a group is customers of a retail operation.

In another embodiment a group is a wholesaler of supplier to a retail operation.

In another embodiment a group is a collaborative group of subjects each with an interest in a specific risk category.

The prospective, personalized risk-adjustment for the consumer further allows the payment options to conform to an individual's healthcare use category based on the analysis of known risk factors and efforts at risk reduction at every stage of risk. In this framework, relating user characteristics to the amount, type and number of risk factors can be tied to the prospective amount, type and duration of services provided during the treatment of a specific disease process, e.g., heart disease, diabetes, hypertension, high cholesterol etc., and based on the ongoing profiling by multivariate risk analysis within the system.

The system and method of the Risk Based Recommender of this example may link the general strategies outlined above with the specific recommendations for products or services from the market that includes retail pharmacy and grocery operations, and e-commerce, based on targeted marketing strategies, including "opt-in" options.

Based on the system analysis of risk category and other data under user control, a filtered array of products, suppliers or services, most relevant to client/customer risk and healthcare guidelines may be displayed by the system.

This type of solution is more efficient than the user's search on the Internet, using general-purpose search engine and hit-or-miss collection of keywords etc. Presenting information to the consumer in this way has the added advantage of presenting it in the most timely and expeditious manner.

The value of identifying and quantifying risk and risk factors is generally obvious to the health clinician, but often not to the individual client. Advising and prioritizing appropriate treatments, and intervening to facilitate modifiable risk factors can significantly reduce the incidence of both first and subsequent events according to the literature. Clarifying these risk factors is regarded as part of standard medical/clinical procedure. Knowing a client's risk factors is a basic piece of the therapeutic puzzle that helps clinicians guide efficacious treatment. Using the new media, such as the Internet, it may be finally be possible to combine user preference models, direct delivery of predictive risk assessment with appropriate classification and personalization of health guidelines to the user, in conjunction with an analysis of those preference models and known risk factors.

Figure 3:
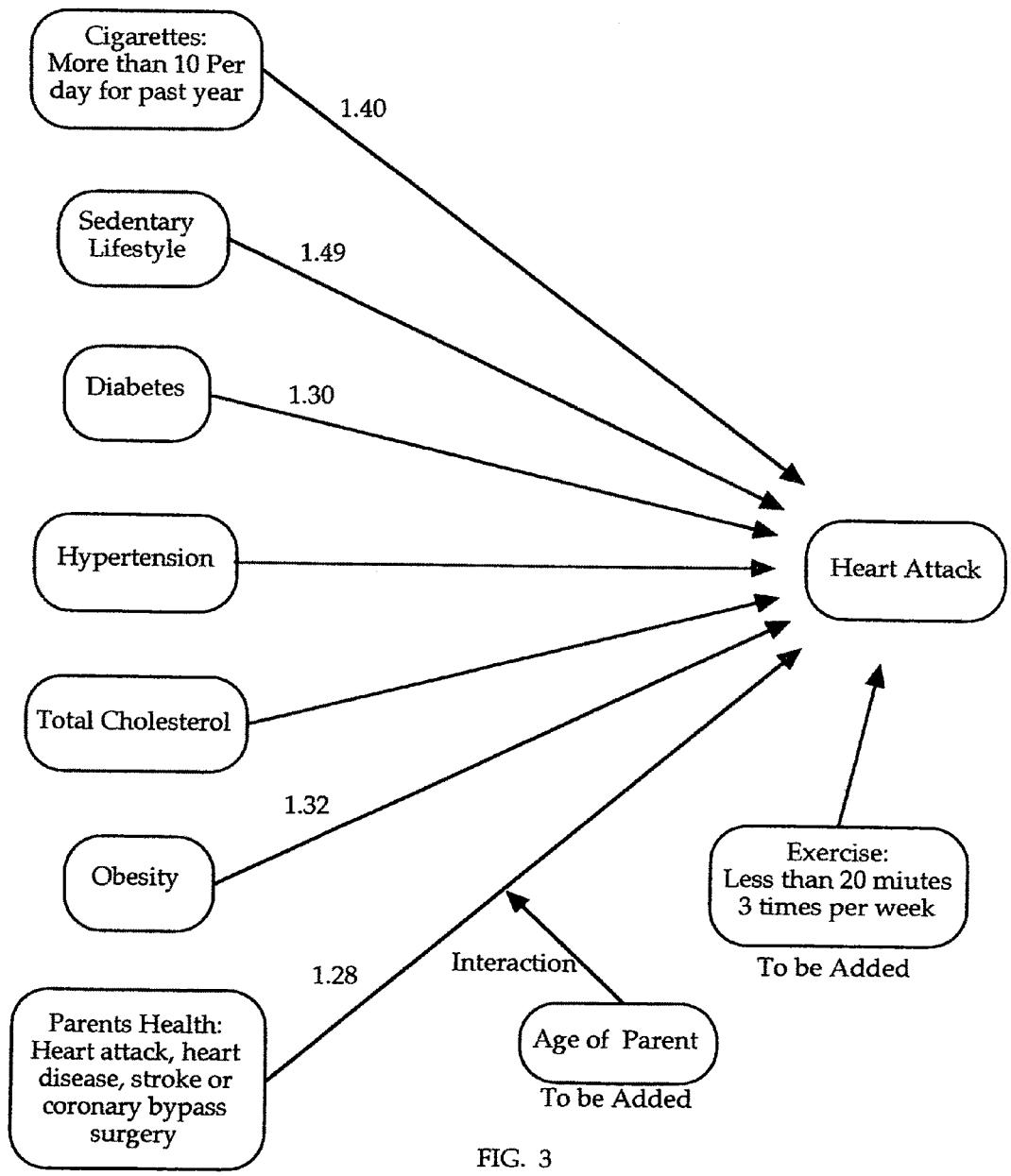
FIG. 3 displays an illustrative map of contributing risk factors to the precipitation of an individual's heart attack.

An instructive example for the use of the system of this example is the "exercise" variable in the LifeStyle Quiz described above. By including exercise as a separate variable, independently measured, tracked and reported, this application of the system of the invention may motivate the consumer to modify a major modifiable risk factor. Exercise has been shown to be an independent risk factor (when population studies are statistically adjusted to account for other risk factors, such as cholesterol, smoking, age, etc., (exercise continues to have an independent effect on mortality). Cf. FIG. 3. We have an "independent" risk factor defined by the epidemiological data, then adding it to any regression equation that predicts risk, will significantly improve the value of the equation.

Many large population studies have identified numerous risk factors for Coronary Artery Disease ("CAD") and also have quantified the "strength" of that association with the risk of having the disease at any given age. It is recognized that in the case of CAD many of the risk factors are modifiable, diet and exercise among them. Therefore, when risk factors are identified, an individual may take intervening steps to reduce or eliminate one or more of them. In most cases, intervention has been shown to reduce the incidence of both first and subsequent events (primary and secondary prevention) in almost all populations.

Figure 7:
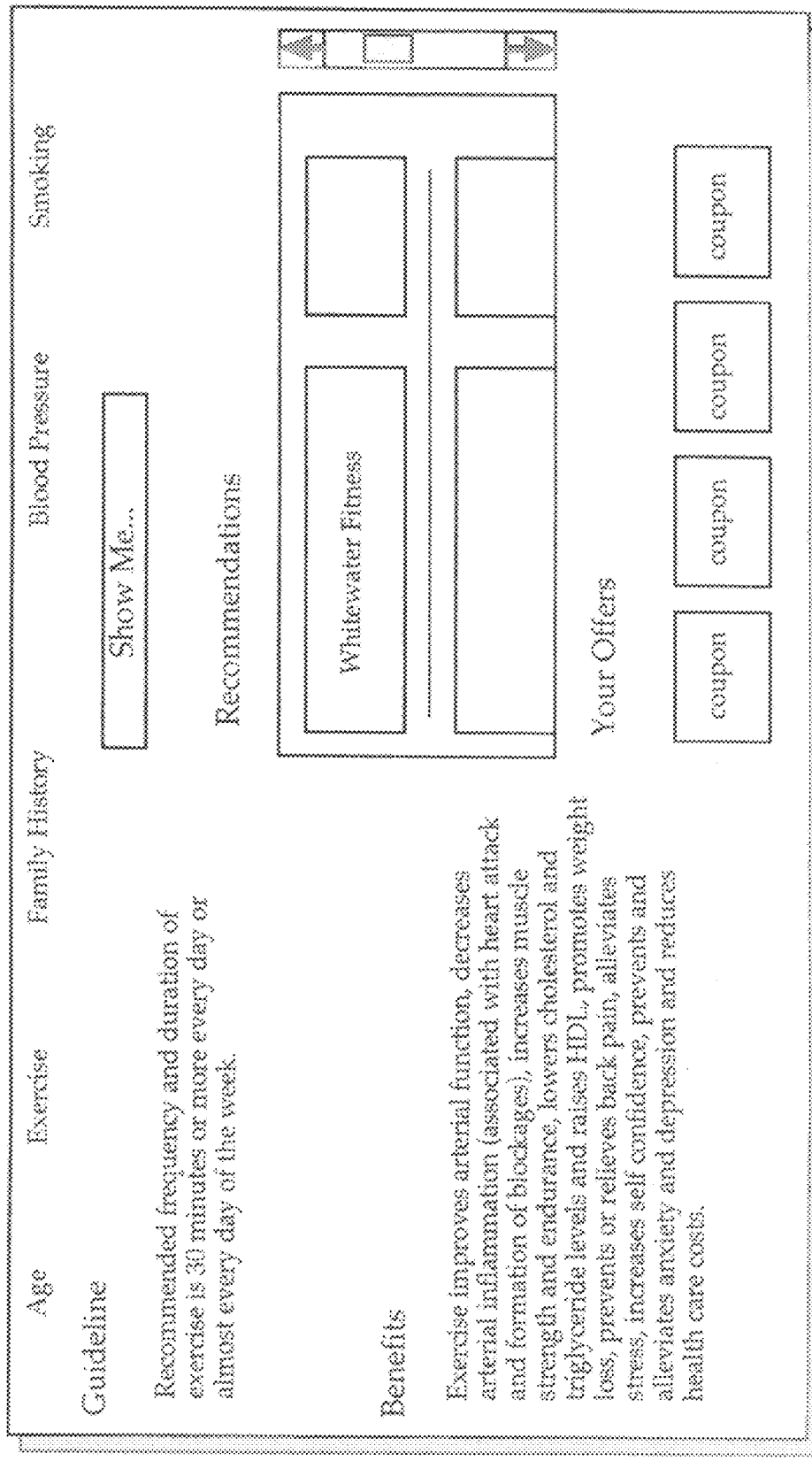
FIG. 7 shows another example of interactive display of product and services integrated with the recommendations.

By focusing on exercise and diet, a personalized recommender system of the invention using the Lifestyle Quiz, along with the appropriate filters and guidelines in the system and integrated with information on products and services, it is possible to impact an individual user's chances of developing CAD by making specific recommendations such as those illustrated in FIG. 7.

Having described the system and the method of creating a comprehensive recommender,

We claim:

1. A computerized method of personalization of healthcare management, comprising the following steps:

providing a database of one or more diseases;
providing a set of variables or parameters correlated to said one or more diseases for which an individual person's values are determinable;
providing one or more computer implemented formulas or algorithms, which accept as input an individual person's values for said set of variable parameters and calculate as output one or more measures of the individual person's predisposition for developing one or more of said one or more diseases;
determining values of said set of variable parameters for a specific individual person;
calculating one or more measures for developing one or more of said one or more diseases by said computer implemented formulas or algorithms and said values of variable parameters for said specific individual person;
incorporating a validation of the calculated one or more measures against computerized database of specific individual person's population cohort;
generating and maintaining a computerized record of said specific individual person's measures of predisposition for developing one or more of said one or more diseases;
maintaining a computerized time dependent series of records of said specific individual person's values and measures of predisposition for developing one or more of said one or more diseases; and
comparing said two or more time dependent series of records of said specific individual person's values and measures of predisposition for developing one or more of said one or more diseases.

2. The method of claim 1 with the following additional step:
providing the display of said specific individual person's computerized record to said specific individual person.

3. The method of claim 1 with the following additional step: providing the display of said specific individual person's computerized record to a party expressly authorized by said specific individual person.

4. The method of claim 1 wherein said computerized record is generated and maintained on a network of computers.

5. The method of claim 1 wherein said time dependent series of records is based on a baseline of said specific individual person's values for said set of variable parameters and generating computerized record of said specific individual person's measures of predisposition for developing one or more of said one or more diseases.

6. The method of claim 1 wherein said one or more diseases include Coronary Artery Disease.

7. The method of claim 6 wherein said algorithm includes the computational result of LIFESTYLE QUIZ™.

8. A system for computer-assisted personalized healthcare management, comprising
a processor and a memory including the following elements;
a database storing one or more diseases;
a set of variable parameters correlated to said one or more diseases for which an individual person's values are determinable;
one or more computer implemented formulas or algorithms, which accept as input an individual person's values for said set of variable parameters and return as output one or more measures of the individual person's predisposition for developing one or more of said one or more diseases;
one or more system components including the means for:

determining values of said set of variable parameters for a specific individual person;

calculating said one or more measures for said individual person for developing one or more of said one or more diseases by said computer implemented formulas or algorithms and said values of variable parameters;

incorporating a validation of the calculated one or more measures against a computerized database of specific individual person's population cohort;

generating and maintaining a computerized record of said specific individual person's measures of predisposition for developing one or more of said one or more diseases;

maintaining a computerized time dependent series of records of said specific individual person's values and measures of predisposition for developing one or more of said one or more diseases; and comparing said two or more time dependent series of records of said specific individual person's values and measures of predisposition for developing one or more of said one or more diseases.

9. The system of claim 8, further comprising a database of prescribed health recommendations for reducing said specific individual person's predisposition for developing one or more of said one or more diseases.

10. The system of claim 8, further comprising at least one database of products or services from which a personalized subset of products and services may be extracted for the use of said specific individual person.

11. The system of claim 10, comprising one or more items to incentivize said individual person to use said products or services.

* * * * *